United States Patent
Nurse et al.

(10) Patent No.: US 9,050,475 B2
(45) Date of Patent: Jun. 9, 2015

(54) HIGH SPF SUNSCREEN COMPOSITIONS

(75) Inventors: Kathryn Nurse, Diego Martin (TT); Ni'Kita Wilson, Union, NJ (US); Xiaodong (David) Lu, Loudonville, NY (US); Irwin Palefsky, West Orange, NJ (US)

(73) Assignee: MD SOLARSCIENCES CORP., Norwalk, CT (US)

( * ) Notice: Subject to any disclaimer, the term of this patent is extended or adjusted under 35 U.S.C. 154(b) by 32 days.

(21) Appl. No.: 13/576,999

(22) PCT Filed: Feb. 9, 2011

(86) PCT No.: PCT/US2011/024128
§ 371 (c)(1),
(2), (4) Date: Oct. 11, 2012

(87) PCT Pub. No.: WO2011/100275
PCT Pub. Date: Aug. 18, 2011

(65) Prior Publication Data
US 2013/0028853 A1    Jan. 31, 2013

Related U.S. Application Data

(60) Provisional application No. 61/302,782, filed on Feb. 9, 2010.

(51) Int. Cl.
*A61K 8/37* (2006.01)
*A61Q 17/04* (2006.01)
*A61K 8/35* (2006.01)
*A61K 8/40* (2006.01)
*A61K 8/85* (2006.01)

(52) U.S. Cl.
CPC . *A61Q 17/04* (2013.01); *A61K 8/35* (2013.01); *A61K 8/37* (2013.01); *A61K 8/40* (2013.01); *A61K 8/85* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 5,505,935 A | 4/1996 | Guerrero et al. | |
| 6,409,997 B1 * | 6/2002 | Castro | 424/59 |
| 2005/0249690 A1 | 11/2005 | Rojas-Wahl et al. | |
| 2007/0298000 A1 | 12/2007 | Grune | |
| 2009/0039322 A1 * | 2/2009 | Bonda et al. | 252/589 |
| 2009/0068130 A1 | 3/2009 | Spaulding et al. | |
| 2009/0068255 A1 | 3/2009 | Yu et al. | |
| 2009/0155371 A1 * | 6/2009 | Sojka et al. | 424/497 |
| 2009/0202459 A1 * | 8/2009 | Spaulding | 424/60 |
| 2012/0045493 A1 * | 2/2012 | Popoff et al. | 424/401 |

FOREIGN PATENT DOCUMENTS

| WO | WO 98/23254 | * | 6/1998 |
|---|---|---|---|
| WO | WO 2009/082511 | * | 7/2009 |

OTHER PUBLICATIONS

Sutton "CDC: Americans Carry Body Burden of Toxic Sunscreen Chemical. Caving to industry, FDA delays safety standards for decades" from the Environmental Working Group website, Mar. 25, 2008 http://www.ewg.org/analysis/toxicsunscreen.*
Truth in Aging website article "diisopropyl adipate" dated Feb. 27, 2009 http://www.truthinaging.com/ingredients/disopropyl-adipate.*
Truth in Aging website article "tetrahexyldecyl ascorbate" dated Sep. 9, 2009 http://www.truthinaging.com/ingredients/tetrahexyldecyl-ascorbate.*
Truth in Aging website article "C12-C15 alkyl benzoate" dated Jan. 1, 2006 http://www.truthinaging.com/ingredients/c12-15-alkyl-benzoate.*
Truth in Aging website article "caprylyl methicone" dated Jan. 1, 2006 http://www.truthinaging.com/ingredients/caprylyl-methicone.*
happi's "Broad Spectrum SPF 33 Sunscreen Spray" of the Sep. 2008 formulary; http://shows.happi.com/formulary/2008/09/.*
Shaath "SPF Boosters & Photostability of Ultraviolet Filters" published Oct. 1, 2007; http://www.happi.com/contents/view_features/2007-10-01/spf-boosters--photostability-of-ultraviolet-f/.*
Google date for Shaath, printed 2014.*
Farris "Topical Vitamin C: a useful agent for treating photoaging and other dermatological conditions," Dermatologic Surgery 31:814-818, 2005.*
Abney et al. "Saving your student's skin. Undergraduate experiments that probe UV protection by sunscreens and sunglasses," Journal of Chemical Education 75(6):757-760, 1998.*
Chaudhuri et al. "Design of a photostabilizer having built-in antioxidant functionality and its utility in obtaining broad-spectrum sunscreen formulations," Photochemistry and Photobiology 82(3):823-828, 2006.*
International Search Report for International Application No. PCT/US11/24128 dated Apr. 4, 2011.
Written Opinion of the International Searching Authority of PCT/US11/24128 dated Apr. 4, 2011.

* cited by examiner

*Primary Examiner* — David J Blanchard
*Assistant Examiner* — Alissa Prosser
(74) *Attorney, Agent, or Firm* — Abelman, Frayne & Schwab

(57) ABSTRACT

Methods and composition for the protection of an object from UV light are provided. For example, in certain aspects, the composition can include a plurality of photo stabilizers that enhance SPF values of the composition. Furthermore, the invention provides for the use of the compositions.

7 Claims, No Drawings

US 9,050,475 B2

HIGH SPF SUNSCREEN COMPOSITIONS

CROSS-REFERENCE TO RELATED APPLICATIONS

This application is a National Phase of PCT/US2011/024128, filed Feb. 9, 2011 which claims priority from U.S. Provisional Application No. 61/302,782, filed Feb. 9, 2010, both of which are incorporated herein by reference.

BACKGROUND OF THE INVENTION

1. Field of the Invention

The present invention generally relates to sunscreen compositions that are suitable for topical application to human skin and hair. More particularly, the present invention relates to photostabilized sunscreen compositions having high sun protection factor (SPF) and high UV-A protection.

2. Description of Related Art

The damaging effects of sunlight on human skin have long been noted. In general terms, harmful ultra-violet (UV) rays, particularly those originating from sunlight, which penetrate the upper atmosphere and reach the earth's surface can be classified into two types: (i) high energy UV-B rays (290-320 nm wavelength) which are absorbed just above the dermis and are responsible for sunburn and tanning effects; and (ii) low energy UV-A rays (320-400 nm wavelength) which penetrate deeper into the skin (to the dermis and beyond), and which cause damaging effects that are more long term in nature, such as skin ageing. Continued skin damage resulting from unprotected exposure to ultraviolet radiation can cause more serious conditions such as, for example, skin cancer. Depending on weather conditions, even casual unprotected exposure to the sun's ultraviolet radiation can be detrimental to one's skin. Accordingly, it is generally recommended that a sunscreen product be applied to the skin before exposure to ultraviolet radiation.

Sunscreen compositions or formulations may be applied directly to the skin to combat sunburning of the skin and the numerous damaging effects resulting from exposure to the sun. When a sunscreen formulation, utilizing the proper sun protection factor (SPF, which is a measure of the protection from the sun afforded by a sunscreen agent or composition) is applied uniformly to the body, sunscreens can be highly effective in protecting against sunburn and damage that can lead to photoaging.

However, to the inventors' knowledge, prior formulations were not able to achieve a photostable sunscreen system with a low level of U.S. FDA approved sunscreens while still providing a high SPF and a high UV-A protection level. Therefore, there remains a need to develop novel methods and compositions for high SPF sun protection.

SUMMARY OF THE INVENTION

Aspects of the present invention overcome a major deficiency in the art by providing novel compositions that provide a high SPF and a high UV-A protection level by using sun screen agents with no or few health risks. Prior sunscreen formulations with high SPF values usually comprise oxybenzone or octinoxate (octyl methoxycinnamate). For example, oxybenzone may boost SPF value by its absorption of short wave UV-A rays. However, there is some evidence, largely arising from correlational studies and in vitro experiments, that particular sunscreen ingredients such as oxybenzone, benzophenone, or octinoxate may cause safety concerns, for example being linked to increased risks of malignant melanoma, a rarer but more deadly form of skin cancer.

Accordingly, in a first embodiment there is provided a topically applicable cosmetic/dermatological high SPF UV-screening composition comprising: (a) a sunscreen; (b) an SPF enhancer comprising a plurality of photostabilizers; and (c) a dermatologically acceptable vehicle. Such a composition may provide unexpectedly high SPF values by a unique combination of photo stabilizers.

In certain aspects, the sunscreen may comprise organic sunscreen agents and/or inorganic sunscreen agents. Oxybenzone and octinoxate are widely used in current high SPF formulations; however, they have safety concerns. Consequently, some embodiments exclude either or both of oxybenzone and octinoxate.

Non-limiting examples of organic sunscreen agents may include octisalate, avobenzone, octocrylene, meradimate, phenylbenzimidazole sulfonic acid (ensulizole), sulisobenzone, and trolamine salicylate. In certain aspects, the composition may comprise avobenzone, octisalate, and/or octocrylene. For example, the composition may include about 2.00%-3.00% (w/w) of avobenzone, about 2.50%-5.00% (w/w) of octisalate, and/or about 2.50%-10.00% of octocrylene. In particular aspects, the composition may comprise avobenzone for UV-A protection. In certain aspects, the composition may be essentially free of inorganic sunscreen agents.

In other aspects, the composition may further include inorganic sunscreen agents such as titanium dioxide and/or zinc oxide. For example, the composition may comprise titanium oxide of about 1.25%-1.45% (w/w) and/or zinc oxide of about 9.25%-11.25% (w/w). The composition may further comprise about 3.15%-3.85% (w/w) of meradimate, about 3.15%-3.85% (w/w) of octisalate, and/or about 9.00%-10.00% of octocrylene.

To improve the aesthetic feel of the inorganic sunscreen agents, the composition may further comprise at least one aesthetic enhancer. An example of such an aesthetic enhancer includes a carboxylated acrylic polymer, particularly, such a polymer having a molecular weight of at least or about 100, 200, 300, 400, 500, 600, 1000 daltons or any range derivable therein, for example, DERMACRYL® 79 polymer.

The sunscreen may be a broad-spectrum sunscreen. A "broad-spectrum sunscreen," as used herein, refers to a sunscreen that blocks at least UV-A and UV-B rays. The compositions of the present invention can diffract or block a broad spectrum of electromagnetic radiation. For example, the compositions can block UV-A, UV-B, UV-C radiation and/or any combination thereof. For example, a composition can be designed to block UV-B radiation but not UV-A radiation. As discussed throughout this specification, a composition can be designed to block and allow a wide range of different electromagnetic ranges (including, for example, ranges within the UV-A, UV-B and UV-C radiation ranges). By way of example only, the compositions can be designed to block electromagnetic radiation having a wavelength of about 200 to about 400, 250 to about 350, 300 to about 325, 200 to about 290, 290 to about 320, or to about 760 to about 2,500 nm. In other aspects, the compositions can permit transmission of a predetermined wavelength range of electromagnetic radiation. Examples of electromagnetic radiation that is not diffracted can include radiation having a wavelength of about 321 to about 400, 290 to about 315, 309 to about 314, or 1660 to about 1900 nm.

In certain embodiments, the composition may include, particularly in the absence of oxybenzone and octinoxate, an SPF enhancer that is effective for enhancing the SPF value of the sunscreen or the composition to at least or about 30, 35, 40, 45, 50, or any range derivable therein. The SPF enhancer may comprise a combination of photostabilizers, antioxidants, or water-resistant film formers. Such an SPF enhancer may provide unexpected SPF enhancement of, for example, at least or about 1.5 times, two times, 2.5 times, three times, 3.5 times, four times, 4.5 times, five times, or any range derivable therein.

Non-limiting examples of photostabilizers may include polyester-8, diethylhexyl syringylidene malonate, and/or butyloctyl salicylate. The photostabilizers may include at least two or three selected from the examples supra. In certain embodiments, the photostabilizers may include two, three, or four selected from the group consisting of polyester-8, diethylhexyl syringylidene malonate, octocrylene, and butyloctyl salicylate. For example, the composition may comprise polyester-8 and octocrylene, and may optionally further comprise diethylhexyl syringylidene malonate and butyloctyl salicylate. In certain aspects, the composition may comprise polyester-8, diethylhexyl syringylidene malonate and butyloctyl salicylate. For example, the composition may comprise at least or about 1% to about 15% (by total weight of the composition) of polyester-8. In another example, the composition may comprise at least or about 1% to about 15% (by total weight of the composition) of diethylhexyl syringylidene malonate.

In a further embodiment, the composition or the SPF enhancer may comprise additional ingredients, such as an antioxidant and/or a film forming agent for SPF enhancement. For example, the antioxidant may be tetrahexyldecyl ascorbate, butylated hydroxytoluene (BHT), or any other antioxidants known in the field. Non-limiting examples of the film forming agents may include acrylates/octylacrylamide copolymer, acrylates copolymer, acrylates/C12-22 alkyl methacrylate copolymer, and a combination thereof. Without wishing to be bound by theory, the inventors contemplate that the film forming agents may enhance SPF values by the water resistance properties.

In a particular embodiment, the composition may be anhydrous. In certain aspects, the composition may comprise water or any solvent of less than or about 0.1%, 0.5%, 1%, 2%, 5%, 10%, or any range derivable therein. The compositions of the present invention can be transparent. The compositions can also be formulated into a sunscreen composition that is applied to skin. The compositions can also be formulated to be spread or sprayed onto the skin. The compositions can be included into a vehicle. The vehicle can include an emulsion, a cream, a lotion, a solution, an anhydrous base, a gel, a spray, or an ointment. The vehicle can be a cosmetic vehicle. The compositions can also be included in a product. The product, in non-limiting embodiments, can be a skin sunscreen product, a skin care product, a sunless skin tanning product, paint, ink, a glass coating, glass, cloth, plastic, or eye glasses, or other products known to those of ordinary skill in the art or identified throughout this specification. In certain aspects, the composition may be formulated as a spray, a stick, an emulsion, a cream, a lotion, a solution, an anhydrous base, a gel, a spray, or an ointment.

Compositions of the present invention may include other beneficial agents and compounds such as, for example, diluents, acute or chronic moisturizing agents (including, e.g., humectants, occlusive agents, and agents that affect the natural moisturization mechanisms of the skin), emollients, anti-irritants, vitamins, structuring agents, pharmaceutical ingredients, trace metals, anti-microbial agents, botanical extracts, fragrances, dyes and color ingredients, structuring agents, thickening agent (thickeners and gelling agents), and/or emulsifiers (see U.S. Pat. No. 6,290,938).

In particular embodiments, the composition can include any one of the following ingredients: alcohol; diisopropyl adipate; cyclopentasiloxane; caprylic/capric triglyceride; or any combination thereof. In certain aspects, the composition can include at least two, three, four, or all of the ingredients identified in the previous sentence. In still other embodiments, the composition can include any one of the following ingredients: petrolatum; shea butter; *copemicia cerifera* (carnauba) wax; jojoba butter; candelilla wax or its substitute; beeswax; $C_{12-15}$ alkyl benzoate; caprylyl methicone; or any combination thereof. In certain aspects, the composition can include at least two, three, four, five, six, seven, or all of the ingredients identified in the previous sentence.

Also disclosed in the present invention is a method of protecting an object from ultraviolet radiation comprising applying on the surface of the object or incorporating into the object the compositions of the present invention. The composition can be topically applied to the object. The object can be skin, hair, or fingernails (including human and animal skin, hair, or fingernails). In certain aspects, the composition can be formulated for application at least once, twice, three, four, five or more times a day to the skin. In other aspects, the composition is sprayed, spread, or rubbed onto the object. The composition in certain embodiments, can be incorporated into the object. The object, by way of example only, can be any article of manufacture known to those of skill in the art or identified in this specification. For example, the object can be paint, ink, windows, self adhesive tap, eye wear (including eye glasses and contact), cloths (including clothing, car covers, boat covers), wood, protective coatings (e.g., water sealers, stains, etc.) or plastics.

Another aspects of the present invention discloses a method of making a composition comprising a sunscreen and an SPF enhancer, wherein the SPF enhancer may include a plurality of photostabilizers, the method comprising (i) obtaining a plurality of photostabilizers; (ii) obtaining a sunscreen; and (iii) admixing (i) and (ii), wherein the admixture is formulated into a composition. For example, the admixing may comprise heating the mixture at a temperature higher than room temperature, such as at least or about 30 to about 100° C., or any range derivable therein.

Also disclosed is a kit comprising the compositions of the present invention. The compositions can be included in a container. In non-limiting aspects, the container can be a bottle, a dispenser, or a package. In certain embodiments, the container can dispense a pre-determined amount of the composition. The composition can be dispensed in a spray, an aerosol, or in a liquid form or semi-solid form. In certain aspects, the container can include indicia on its surface. The indicia, for example, can be a word, a phrase, an abbreviation, a picture, or a symbol. The word or phrase can be "sunscreen," "sunblock," "UV specific sunblock," etc.

In another embodiment, there is disclosed a product or article of manufacture comprising the compositions of the present invention. Product and articles of manufacture that are contemplated as being useful with the present invention are those known to a person of ordinary skill in the art and those identified in this specification. Non-limiting examples include sunscreen products, sunblock products, cosmetic products (e.g., sunless tanning product, moisturizers, creams, lotions, skin softeners, foundations, night creams, lipsticks, cleansers, toners, masks, and other make-up products), paint, ink, cloths (e.g., clothing, tarps, car and boat covers, ext.), glass, glass films, eye ware (e.g., eye glasses and contacts), coatings, windows, plastics, ext.

Embodiments discussed in the context of methods and/or compositions of the invention may be employed with respect to any other method or composition described herein. Thus, an embodiment pertaining to one method or composition may be applied to other methods and compositions of the invention as well.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

The use of sunblock compositions have gained more and more popularity over the years. For example, sunblock compositions can be used to protect a person's skin, hair, or an article of manufacture from the sun's or artificial electromagnetic radiation. A problem associated with previous sunblock compositions, however, is their inability to have high SPF values (more than 30) without using oxybenzone or octinoxate that may have potential health risks.

In accordance with certain aspects of the present invention, there are provided compositions that have several advantages over previous compositions. The disclosed compositions, in non-limiting aspects, include a plurality of photostabilizers that provide an unexpected SPF enhancement without the need to use oxybenzone or octinoxate. The compositions can be used to protect, for example, a person's skin, hair, or an article of manufacture from damaging electromagnetic radiation such as UV.

These and other aspects of the present invention are described in further detail in the following sections.

I. Sunscreen Agents

There are currently 17 active ingredients approved by the FDA for use in sunscreens. These filters fall into two broad categories: organic/chemical and inorganic/physical. Most UV filters are organic: They form a thin, protective film on the surface of the skin and absorb the UV radiation before it penetrates the skin. The inorganic sunscreens are insoluble particles that reflect UV away from the skin. The composition of the present invention may contain a mixture of organic and inorganic active ingredients or only organic active ingredients.

UV absorption agents that can be used in combination with the compositions of the present invention include inorganic and organic sunblocks. Non-limiting examples of organic sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate.

For minimizing potential health risks, particular aspects of the composition may exclude the use of high risk sunscreen agents such as para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), and cinnamate ester.

Non-limiting examples of inorganic sunblocks include metal oxides (e.g., titanium dioxide and zinc oxide).

The compositions can have a sun protection factor (SPF) of 2, 3, 4, 5, 6, 7, 8, 9, 10, 11, 12, 13, 14, 15, 20, 25, 30, 35, 40, 45, 50, 55, 60, 70, 80, 90 or more, or any integer or derivative therein.

Compositions of the present invention can have UV-A and UV-B protection properties. For example, the composition can comprise one or more sunscreen agents that have UV-A protection properties, one or more sunscreen agents that have UV-B protection properties, and/or one or more sunscreen agents that have both UV-A and UV-B protection properties. Table 1 describes known UV-A or UV-B protection properties of FDA-approved sunscreens.

TABLE 1

| FDA-Approved Sunscreens FDA-Approved Sunscreens | |
| --- | --- |
| Active Ingredient/UV Filter Name | Range Covered |
| Chemical/organic absorbers: | UV-A1: 340-400 nm<br>UV-A2: 320-340 nm<br>UV-B: 290-320 nm |
| Aminobenzoic acid (PABA) | UV-B |
| Avobenzone | UV-A1 |
| Cinoxate | UV-B |
| Dioxybenzone | UV-B, UV-A2 |

TABLE 1-continued

FDA-Approved Sunscreens
FDA-Approved Sunscreens

| Active Ingredient/UV Filter Name | Range Covered |
|---|---|
| Ensulizole (Phenylbenzimiazole Sulfonic Acid) | UV-B |
| Homosalate | UV-B |
| Meradimate (Menthyl Anthranilate) | UV-A2 |
| Octocrylene | UV-B |
| Octinoxate (Octyl Methoxycinnamate) | UV-B |
| Octisalate (Octyl Salicylate) | UV-B |
| Oxybenzone | UV-B, UV-A2 |
| Padimate O | UV-B |
| Sulisobenzone | UV-B, UV-A2 |
| Trolamine Salicylate | UV-B |
| Titanium Dioxide | UV-B, UV-A2 |
| Zinc Oxide | UV-B, UV-A2, UV-A1 |

For a product marketed in the United States, preferred cosmetically-acceptable photoactive compounds and concentrations (reported as a percentage by weight of the total cosmetic sunscreen composition) include: aminobenzoic acid (also called para-aminobenzoic acid and PABA; 15% or less), avobenzone (also called butyl methoxy dibenzoylmethane; 3% or less), cinoxate (also called 2-ethoxyethylp-methoxycinnamate; 3% or less), dioxybenzone (also called benzophenone-8; 3% or less), homosalate (15% or less), menthyl anthranilate (also called menthyl 2-aminobenzoate; 5% or less), octocrylene (also called 2-ethylhexyl-2-cyano-3.3 diphenylacrylate; 10% or less), octyl salicylate (also called 2-ethylhexyl salicylate; 5% or less), padimate 0 (also called octyl dimethyl PABA; 8% or less), phenylbenzimidazole sulfonic acid (water soluble; 4% or less), sulisobenzone (also called benzophenone-4; 10% or less), titanium dioxide (25% or less), trolamine salicylate (also called triethanolamine salicylate; 12% or less), and zinc oxide (25% or less).

For a product marketed in the European Union, preferred cosmetically-acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine (10% or less, also called TINOSORB S).

II. SPF Enhancers

In certain aspects of the invention, an SPF enhancer comprising a plurality of photostabilizers may be used for the unexpected enhancement of SPF values of the composition. The SPF enhancer may also comprise antioxidants or thickening agents (film formers).

A. Photostabilizers

Photostabilizers are primarily used to reduce the breakdown of sunscreens under prolonged exposure to UV light. However, they are found to provide unexpectedly high SPF values when used in the compositions and methods of the present invention.

In certain aspects, photostabilizers are organic compounds that help to prevent sunscreen agents from losing their effectiveness in sunlight. Some of them help to stabilize the molecules of sunscreen agents structurally and geometrically through electrostatic and van der Waals interactions, which makes them less likely to take part in chemical reactions. Another type of photostabilizer protects sunscreen agents by helping to dissipate the energy from UV more quickly, thus reducing or even eliminating the possibility of a chemical reaction. This process is called energy transfer, and it can take place when the UV filter and photostabilizer molecules exchange electrons, or even by action at a distance, as a radio transmitter sends a signal to a nearby receiver. In this way, the sunscreen agents are freed up to protect the skin by absorbing the harmful rays, while the photostabilizers dispose of the energy.

In a particular aspect, the composition may include avobenzone for the UV-A protection. Avobenzone has been shown to degrade significantly in light, resulting in less protection over time. The UV-A light in a day of sunlight in a temperate climate is sufficient to break down most of the compound. Data presented to the Food and Drug Administration by the Cosmetic, Toiletry and Fragrance Association indicates a −36% change in avobenzone's UV absorbance following one hour of exposure to sunlight. This degradation can be reduced by using a photo stabilizer, like octocrylene. Other photostabilizers include: 4-Methylbenzylidene camphor (USAN Enzacamene); Tinosorb S (USAN Bemotrizinol, INCI Bis-Ethylhexyloxyphenol Methoxyphenyl Triazine); Tinosorb M (USAN Bisoctrizole, INCI Methylene Bis-Benzotriazolyl Tetramethylbutylphenol); Butyloctyl Salicylate (Tradename HallBrite BHB); Hexadecyl Benzoate; Butyloctyl Benzoate; Mexoryl SX (USAN Ecamsule, INCI Terephthalylidene Dicamphor Sulfonic Acid); Corapan TQ (INCI Diethylhexyl 2,6-Naphthalate); Parsol SLX (INCI Polysilicone-15) Oxynex ST (INCI Diethylhexyl Syringylidene Malonate) Polycrylene (INCI Polyester-8); complexing avobenzone with cyclodextrins may also increase its photostability. Two or more of the above photostabilizers may be used in combination to provide the unexpected SPF enhancement effect according to certain aspects of the invention.

Avobenzone can degrade faster in light in combination with mineral UV absorbers like zinc oxide and titanium dioxide, thus currently not allowed in the United States. Consequently, some aspects of the composition may comprise mineral UV absorbers in the absence of avobenzone, with SPF enhancement provided by a combination of photostabilizers such as octocrylene and polyester-8.

B. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thio salicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

C. Thickening Agents

Thickening agents or film formers, including thickeners or gelling agents, include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, 4$^{th}$ Ed., 1991). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

III. Compositions of the Present Invention

A. Combinations and Amounts of Ingredients

It is contemplated that the compositions of the present invention can include a plurality of SPF enhancers include photostabilizers, antioxidants and/or film formers. The compositions can also include additional ingredients described throughout this specification. The concentrations of the SPF enhancers and/or additional ingredients can vary. In non-limiting embodiments, for example, the compositions can include in their final form, for example, at least about 0.0001% to about 99% or more, or any range or integer derivable therein, of at least one of the SPF enhancers or photostabilizers identified in this specification or any combination thereof or additional ingredients. In non-limiting aspects, the percentage of such ingredients can be calculated by weight or volume of the total weight of the compositions. The concentrations can vary depending on the desired effect of the compositions or on the product into which the compositions are incorporated.

B. Composition Vehicles

The compositions of the present invention can be formulated into all types of vehicles. Non-limiting examples of suitable vehicles include emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (both aqueous and hydro-alcoholic), anhydrous bases (such as lipsticks and powders), gels, ointments, pastes, milks, liquids, aerosols, solid forms, or eye jellies. Variations and other appropriate vehicles will be apparent to the skilled artisan and are appropriate for use in the present invention. In certain aspects, the concentrations and combinations of the ingredients can be selected in such a way that the combinations are chemically compatible and do not form complexes which precipitate from the finished product.

It is also contemplated that the SPF enhancers such as photostabilizers, and additional ingredients identified throughout this specification can be encapsulated for delivery to a target area such as skin. Non-limiting examples of encapsulation techniques include the use of liposomes, vesicles, and/or nanoparticles that can be used as delivery vehicles to deliver such ingredients to skin (see, e.g., U.S. Pat. No. 6,387, 398; U.S. Pat. No. 6,203,802; U.S. Pat. No. 5,411,744; Kreuter 1988).

Also contemplated are pharmaceutically-acceptable or pharmacologically-acceptable compositions. The phrase "pharmaceutically-acceptable" or "pharmacologically-acceptable" includes compositions that do not produce an allergic or similar untoward reaction when administered to a human. Typically, such compositions are prepared either as topical compositions, liquid solutions or suspensions, solid forms suitable for solution in, or suspension in, liquid prior to use can also be prepared. Routes of administration can vary with the location and nature of the condition to be treated, and include, e.g., topical, inhalation, intradermal, transdermal, parenteral, intravenous, intramuscular, intranasal, subcutaneous, percutaneous, intratracheal, intraperitoneal, intratumoral, perfusion, lavage, direct injection (e.g., an injectable solution), and oral administration and formulation (e.g., tablets, capsules, etc.).

C. Products

The compositions of the present invention can be incorporated into products. Non-limiting examples of products include cosmetic products, food-based products (e.g., fortified water, energy drinks, nutritional drinks, vitamins, supplements, solid foods), pharmaceutical products, etc. By way of example only, non-limiting cosmetic products include sunscreen products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks and lip balms, cleansers, toners, masks, deodorants, antiperspirants, exfoliating compositions, shaving-related products (e.g., creams, "bracers" and aftershaves), pre-moistened wipes and washcloths, tanning lotions, bath products such as oils, foot care products such as powders and sprays, skin colorant and make-up products such as foundations, blushes, rouges eye shadows and lines, lip colors and mascaras, baby products (e.g., baby lotions, oils, shampoos, powders and wet wipes), and skin or facial peel products. Additionally, the cosmetic products can be formulated as leave-on or rinse-off products.

D. Additional Ingredients

Compositions of the present invention can include additional ingredients. Non-limiting examples of additional ingredients include cosmetic ingredients (both active and non-active) and pharmaceutical ingredients (both active and non-active).

a. Cosmetic Ingredients

The CTFA International Cosmetic Ingredient Dictionary and Handbook (2008), 12$^{th}$ Edition, describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, essential oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes). The following provides specific non-limiting examples of some of the additional ingredients that can be used with the compositions of the present invention.

i. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, aloe barbadensis, aloe-barbadensis extract, aloe barbadensis gel, althea officinalis extract, aluminum starch octenylsuccinate, aluminum stearate, apricot (*prunus armeniaca*) kernel oil, arginine, arginine aspartate, arnica montana extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, calendula officinalis extract, calendula officinalis oil, candelilla (*euphorbia cerifera*) wax, canola oil, caprylic/capric triglyceride, cardamon (*elettaria cardamomum*) oil, carnauba (*copemicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (*oenothera biennis*) oil, fatty acids, tructose, gelatin, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, macadamia ternifolia nut oil, magnesium stearate, magnesium sulfate, maltitol, matricaria (*chamomilla recutita*) oil, methyl glucose sesquistearate, methylsilanol PCA, microcrystalline wax, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

ii. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

iii. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

iv. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In preferred aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

v. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

b. Pharmaceutical Ingredients

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

IV. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, foam, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

V. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

An Example of SPF 40+ Stick Formulation

Table 2 includes a non-limiting example of a composition of the present invention (e.g., SPF 40+ stick) (WT: weight). The composition can be formulated into a stick or any anhydrous formulations. The additional ingredients identified throughout the specification can be included into the Table 2 composition (e.g., by adjusting the emollient or structuring agent content of composition). Further, the concentration ranges of the ingredients identified in Table 2 can vary depending on a desired formulation (e.g., cream, lotion, moisturizer, cleanser, etc.). Table 3 provides a specification of the composition in Table 2. In this example, the formulation may have zinc oxide of about 10.25%, octocrylene of about 10.00%, octisalate of about 3.50%, meradimate of about 3.50%, and titanium dioxide of about 1.35% (all are weight percentages).

TABLE 2

| | | | | | | | |
|---|---|---|---|---|---|---|---|
| Formulation for SPF40+ Stick | | | | | | | |
| NO. | PHASE | INGREDIENT (TRADE NAME) | FUNCTION | INCI DESIGNATION | SUPPLIER | % by WT | Batch size |
| 1 | A | PENRECO SNOW WHITE PETROLATUM USP | EMOLLIENT | PETROLATUM | PENRECO | 10.00 | 200.00 20.00 |
| 2 | A | SHEA BUTTER HMP | EMOLLIENT | BUTYROSPERMUM PARKII (SHEA BUTTER) | EARTH SUPPLIED PRODUCTS | 10.00 | 20.00 |

TABLE 2-continued

| | | | | Formulation for SPF40+ Stick | | | |
|---|---|---|---|---|---|---|---|
| 3 | A | REFINED #1 YELLOW CARNAUBA WAX N.F. | STRUCTURE | COPERNICIA CERIFERA (CARNAUBA) WAX | FRANK B. ROSS | 1.00 | 2.00 |
| 4 | A | PERFORMALENE 400 | STRUCTURE | POLYETHYLENE | UNIVAR | 4.00 | 8.00 |
| 5 | A | ISO JOJOBA 50 | STRUCTURE | SIMMONDSIA CHINENSIS (JOJOBA) BUTTER | DESERT WHALE | 2.00 | 4.00 |
| 6 | A | CANDELILLA WAX SUBSTITUTE DR-415 | STRUCTURE | PARAFFIN WAX COPERNICIA CERIFERA (CARNAUBA) WAX HYDROGENATED SOYBEAN OIL STEARIC ACID MICROCRYSTALLINE WAX | STRAHL & PITSCH | 4.00 | 8.00 |
| 7 | A | WHITE N.F. BLEACHED BEESWAX | STRUCTURE | BEESWAX | FRANK B. ROSS | 8.00 | 16.00 |
| 8 | A | BHT | ANTIOXIDANT | BHT | MERISOL/ACETO | 0.10 | 0.20 |
| 9 | A | FINSOLV TN | EMOLLIENT | C12-15 ALKYL BENZOATE | INNOSPEC | 3.00 | 6.00 |
| 10 | B | DC TORAY FZ-3196 | EMOLLIENT | CAPRYLYL METHICONE | DOW CORNING | 16.39 | 32.78 |
| 11 | B | UVINUL N539T | SUNSCREEN | OCTOCRYLENE | BASF | 10.00 | 20.00 |
| 12 | B | ESCALOL 587 | SUNSCREEN | ETHYLHEXYL SALICYLATE (OCTISALATE) | ISP SUTTON | 3.50 | 7.00 |
| 13 | B | NEO HELIOPANMA | SUNSCREEN | MENTHYL ANTHRANILATE (MERADIMATE) | SYMRISE | 3.50 | 7.00 |
| 14 | B | POLYCRYLENE | SUNSCREEN BOOSTER | POLYESTER-8 | HALLSTAR | 1.00 | 2.00 |
| 15 | B | SPD-Z5 | SUNSCREEN | ZINC OXIDE CYCLOPENTASILOXANE POLYGLYCERYL-3 POLYDIMETHYLSILOXYETHYL DIMETHICONE TRIETHOXYSILYLETHYL POLYDIMETHYLSILOXYETHYL HEXYL DIMETHICONE | SHIN-ETSU | 18.50 | 37.00 |
| 16 | B | SPD-T5 | SUNSCREEN | CYCLOPENTASILOXANE TITANIUM DIOXIDE POLYGLYCERYL-3 POLYDIMETHYLSILOXYETHYL DIMETHICONE ALUMINUM HYDROXIDE STEARIC ACID | SHIN-ETSU SILICONES | 5.00 | 10.00 |
| 17 | C | BV-OSC | ANTIOXIDANT | TETRAHEXYLDECYL ASCORBATE | BARNET | 0.01 | 0.02 |
| | | TOTAL | | | | 100.00 | 200.00 |

| | MANUFACTURING INSTRUCTIONS: |
|---|---|
| PHASE A | COMBINE PHASE A INGREDIENTS. HEAT WHILE MIXING TO 90° C. |
| PHASE B | COMBINE PHASE B INGREDIENTS AND HEAT WITH MIXING TO 85 C. |
| PHASE C | SLOWLY ADD PHASE B TO PHASE A WITH MIXING. HOMOGENIZE AT 5000 RPM FOR 3 MINUTES COOL WITH MIXING TO 80° C. ADD PHASE C TO BATCH AT 75-80° C., MIX AND POUR INTO MOLD |

TABLE 3

| Product Control Specification (SPF 40+ Stick) | | | |
|---|---|---|---|
| TEST | INSTRUMENT | CONDITIONS | RANGE |
| APPEARANCE | VISUAL | N/A | OFF WHITE SLIGHT STRAW COLORED STICK-TO MATCH STANDARD |
| ODOR | ORGANOLEPTIC | N/A | TO MATCH STANDARD |
| CONE PENETRATION | | 25° C. | 90-120 |
| % SUNSCREEN | | | TiO2- 1.25%-1.45% ZnO - 9.25%-11.25% Octocrylene - 9.00%-11.00% Octisalate- 3.15%-3.85% Meradimate- 3.15%-3.85% |

TABLE 3-continued

| | Product Control Specification (SPF 40+ Stick) | | |
|---|---|---|---|
| TEST | INSTRUMENT | CONDITIONS | RANGE |
| BACTERIOLOGY | USP STANDARD PLATE COUNT | | Less than 10 cfu mould/g Less than 10 cfu bacteria/g No Pathogens |

Example 2

An Example of SPF 40+ Spray Formulation

Table 4 includes a non-limiting example of a composition of the present invention (e.g., SPF 40+ spray). The composition can be formulated into a spray or any anhydrous formulations. The additional ingredients identified throughout the specification can be included into the Table 4 composition (e.g., by adjusting the emollient or diluent content of composition). Further, the concentration ranges of the ingredients identified in Table 5 can vary depending on a desired formulation (e.g., cream, lotion, moisturizer cleanser, etc.). Table 5 provides a specification of the composition in Table 4. In this example, the formulation may have octocrylene of about 2.75%, octisalate of about 5.00%, and avobenzone of about 3.00% (all are weight percentages).

TABLE 4

| | | | Formulation for SPF40+ Spray | | | | |
|---|---|---|---|---|---|---|---|
| NO. | PHASE | INGREDIENT (TRADE NAME) | FUNCTION | INCI DESIGNATION | SUPPLIER | % BY WT | Batch Size |
| 1 | A | SD ALCOHOL 40 200 PROOF | DILUENT | SD ALCOHOL 40 | LYONDEL/ EQUASTAR | 61.25 | 500.00 306.25 |
| 2 | A | DERMACRYL 79 | FILM FORMER | ACRYLATES/OCTYLACRYLAMIDE COPOLYMER | NAT'L STARCH | 2.50 | 12.50 |
| 3 | B | BV-OSC | ANTIOXIDANT | TETRAHEXYLDECYL ASCORBATE | BARNET | 0.10 | 0.50 |
| 4 | B | CERAPHYL 230 | EMOLLIENT | DIISOPROPYL ADIPATE | ISP SUTTON | 3.00 | 15.00 |
| 5 | B | ESCALOL 587 | SUNSCREEN | ETHYLHEXYL SALICYLATE (OCTISALATE) | ISP SUTTON | 5.00 | 25.00 |
| 6 | B | NEO HELIOPAN 357 | SUNSCREEN | BUTYL METHOXYDIBENZOLMETHANE (AVOBENZONE) | SYMRISE | 3.00 | 15.00 |
| 7 | B | UVINUL N539T | SUNSCREEN | OCTOCRYLENE | BASF | 2.75 | 13.75 |
| 8 | B | HALLBRITE BHB | SUNSCREEN STABILIZER/EMOLLIENT | BUTYLOCTYL SALICYLATE | RTD HALLSTAR | 8.00 | 40.00 |
| 9 | B | DC 245 FLUID | EMOLLIENT | CYCLOPENTASILOXANE | DOW CORNING/ UNIVAR | 5.00 | 25.00 |
| 10 | B | POLYCRYLENE | SUNCREEN STABILIZER/EMOLLIENT | POLYESTER-8 | HALLSTAR | 6.00 | 30.00 |
| 11 | B | OXYNEX ST LIQUID | ANTIOXIDANT/SPF BOOSTER | DIETHYLHEXYL SYRINGYLIDENE MALONATE CAPRYLIC/CAPRIC TRYGLYCERIDE | EMD | 3.40 | 17.00 |
| | | TOTAL | | | | 100.00 | 500.00 |

| | MANUFACTURING INSTRUCTIONS: |
|---|---|
| PHASE A | DISPERSE DERMACRYL IN ALCOHOL AND MIX UNTIL UNIFORM (20 MINUTES) |
| PHASE B | COMBINE PHASE B INGREDIENTS AND HEAT TO 60 C. WITH MIXING. MAKE SURE ALL POWDERS DISSOLVE ONCE UNIFORM, COOL TO 35 C. THEN SLOWLY ADD PHASE B TO PHASE A |

TABLE 5

| | Product Control Specification (SPF 40+ Spray) | | |
|---|---|---|---|
| TEST | INSTRUMENT | CONDITIONS | RANGE |
| APPEARANCE | VISUAL | N/A | CLEAR/HAZY AMBER COLORED THIN LIQUID-TO MATCH STANDARD |

TABLE 5-continued

Product Control Specification (SPF 40+ Spray)

| TEST | INSTRUMENT | CONDITIONS | RANGE |
|---|---|---|---|
| ODOR | ORGANOLEPTIC | N/A | TO MATCH STANDARD |
| SPECIFIC GRAVITY | ALUMINUM PYCNOMETER | 25° C. | 0.866-0.876 |
| VISCOSITY | | 25° C. TD @5 RPM | WATER THIN LIQUID |
| % SUNSCREEN | | | Avobenzone- 2.70%-3.30% Octisalate- 4.50%-5.50% Octocrylene- 2.50%-3.00% |
| BACTERIOLOGY | USP STANDARD PLATE COUNT | | Less than 10 cfu mould/g Less than 10 cfu bacteria/g No Pathogens |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 2,798,053
U.S. Pat. No. 3,755,560
U.S. Pat. No. 4,421,769
U.S. Pat. No. 4,509,949
U.S. Pat. No. 4,599,379
U.S. Pat. No. 4,628,078
U.S. Pat. No. 4,835,206
U.S. Pat. No. 4,849,484
U.S. Pat. No. 5,011,681
U.S. Pat. No. 5,087,445
U.S. Pat. No. 5,100,660
U.S. Pat. No. 5,411,744
U.S. Pat. No. 6,203,802
U.S. Pat. No. 6,290,938
U.S. Pat. No. 6,387,398
CTFA Cosmetic Ingredient Dictionary, 3$^{rd}$ Ed.
CTFA International Cosmetic Ingredient Dictionary, 4$^{th}$ Ed., 1991.
Kreuter, *J. Microencapsul.*, 5(2):115-27, 1988.
McCutcheon's, Detergents and Emulsifiers, North American Edition, 1986.
The CTFA International Cosmetic Ingredient Dictionary and Handbook, 12$^{th}$ Ed., 2008.

What is claimed is:

1. A topically applicable cosmetic/dermatological UV-screening composition consisting essentially of:
   (a) a broad-spectrum sunscreen that protects against UVA and UVB radiation that includes organic sunscreen agents, wherein the organic sunscreen agents are a mixture of 5%, by weight, of octisalate, 3%, by weight, of avobenzone and 2.75%, by weight, of octocrylene, and are essentially free of oxybenzone and octyl methoxycinnamate (octinoxate);
   (b) an SPF enhancer consisting of 6% by weight polyester-8, and 8% by weight butyloctyl salicylate as photostabilizers, and acrylates/octylacrylamide copolymer as a film former;
   (c) a dermatologically acceptable vehicle, and
   wherein said photostabilizers are present at an amount effective for enhancing the sun protection factor (SPF) value of said sunscreen to at least 40.

2. The composition of claim 1, wherein the composition is anhydrous.

3. The composition of claim 1, wherein the composition is formulated as a spray.

4. A topically applicable cosmetic/dermatological UV-screening composition consisting essentially of:
   (a) a broad-spectrum sunscreen that protects against UVA and UVB radiation that includes organic sunscreen agents, wherein the organic sunscreen agents are a mixture of 5%, by weight, of octisalate, 3%, by weight, of avobenzone and 2.75%, by weight, of octocrylene, and are essentially free of oxybenzone and octyl methoxycinnamate (octinoxate);
   (b) an SPF enhancer consisting of 6% by weight polyester-8, 8% by weight butyloctyl salicylate, and diethylhexyl syringylidene malonate as photostabilizers, and acrylates/octylacrylamide copolymer as a film former;
   (c) a dermatologically acceptable vehicle, and
   wherein said photostabilizers are present at an amount effective for enhancing the sun protection factor (SPF) value of said sunscreen to at least 40.

5. The composition of claim 4, wherein the composition is anhydrous.

6. The composition of claim 4, wherein the composition is formulated as a spray.

7. The composition of claim 4, containing 3.4% by weight diethylhexyl syringylidene malonate.

* * * * *